(12) United States Patent
Ungelenk et al.

(10) Patent No.: US 10,384,990 B2
(45) Date of Patent: Aug. 20, 2019

(54) METHOD FOR PRODUCING 1,3-BUTADIENE BY DEHYDROGENATING N-BUTENES, A MATERIAL FLOW CONTAINING BUTANES AND 2-BUTENES BEING PROVIDED

(71) Applicants: BASF SE, Ludwigshafen (DE); Linde AG, Munich (DE)

(72) Inventors: Jan Ungelenk, Neuhofen (DE); Philipp Grüne, Mannheim (DE); Christian Walsdorff, Ludwigshafen (DE); Jan Pablo Josch, Neustadt (DE); Michael Bender, Ludwigshafen (DE)

(73) Assignees: BASF SE (DE); Linde AG (DE)

( * ) Notice: Subject to any disclaimer, the term of this patent is extended or adjusted under 35 U.S.C. 154(b) by 68 days.

(21) Appl. No.: 15/525,330

(22) PCT Filed: Nov. 9, 2015

(86) PCT No.: PCT/EP2015/076018
§ 371 (c)(1),
(2) Date: May 9, 2017

(87) PCT Pub. No.: WO2016/075065
PCT Pub. Date: May 19, 2016

(65) Prior Publication Data
US 2018/0282246 A1    Oct. 4, 2018

(30) Foreign Application Priority Data
Nov. 14, 2014 (EP) .................................. 14193247

(51) Int. Cl.
*C07C 5/48* (2006.01)
*C07C 2/10* (2006.01)
(Continued)

(52) U.S. Cl.
CPC .................. *C07C 5/48* (2013.01); *C07C 2/06* (2013.01); *C07C 2/10* (2013.01); *C07C 2/56* (2013.01);
(Continued)

(58) Field of Classification Search
CPC .... C07C 5/48; C07C 6/04; C07C 7/08; C07C 7/11; C07C 9/16; C07C 11/06; C07C 11/167; C07C 2/06; C07C 2/56
See application file for complete search history.

(56) References Cited

U.S. PATENT DOCUMENTS 3,911,039 A    10/1975 Grasselli et al.
3,914,332 A    10/1975 Dickason
(Continued)

FOREIGN PATENT DOCUMENTS

CN    101492334 B    11/2012
CN    101492335 B    7/2013
(Continued)

OTHER PUBLICATIONS

Geilen et al. ("Butenes", Ullmann's Encyclopedia of Industrial Chemistry, Published Jan. 31, 2014) (Year: 2014).*
(Continued)

*Primary Examiner* — Brian A McCaig
*Assistant Examiner* — Jason Y Chong
(74) *Attorney, Agent, or Firm* — Drinker Biddle & Reath LLP

(57) ABSTRACT

The invention relates to a process for preparing 1,3-butadiene from n-butenes, comprising the steps of:
A) providing an input gas stream a comprising butanes, 1-butene, 2-butene and isobutene, with or without 1,3-butadiene, from a fluid catalytic cracking plant;
(Continued)

B) removing isobutene from the input gas stream a, giving a stream b comprising butanes, 1-butene and 2-butene, with or without 1,3-butadiene;

C) feeding the stream b comprising butanes, 1-butene and 2-butene and optionally an, oxygenous gas and optionally water vapor into at least one dehydrogenating zone and dehydrogenating 1-butene and 2-butene to 1,3-butadiene, giving a product gas stream c comprising 1,3-butadiene, butanes, 2-butene and water vapor, with or without oxygen, with low-boiling hydrocarbons, with high-boiling secondary components, with or without carbon oxides and with or without inert gases;

D) cooling and compressing the product gas stream c, giving at least one aqueous condensate stream d1 and a gas stream d2 comprising 1,3-butadiene, butanes, 2-butene and water vapor, with or without oxygen, with low-boiling hydrocarbons, with or without carbon oxides and with or without inert gases;

Ea) removing uncondensable and low-boiling gas constituents comprising low-boiling hydrocarbons, with or without oxygen, with or without carbon oxides and with or without inert gases, as gas stream e2 from the gas stream d2 by absorbing the $C_4$ hydrocarbons comprising 1,3-butadiene, butanes and 2-butene in an absorbent, giving an absorbent stream laden with $C_4$ hydrocarbons and the gas stream e2, and Eb) subsequently desorbing the $C_4$ hydrocarbons from the laden absorbent stream, giving a $C_4$ hydrocarbon stream e1;

F) separating the $C_4$ hydrocarbon stream e1 by extractive distillation with a 1,3-butadiene-selective solvent into a stream f1 comprising 1,3-butadiene and the selective solvent and a stream f2 comprising butanes and 2-butene, wherein at least 90% of the 1-butene present in stream b is converted in step C) and a product stream f2 comprising butanes and 2-butene is obtained in step F.

8 Claims, 1 Drawing Sheet

(51) Int. Cl.
- *C07C 2/62* (2006.01)
- *C07C 6/04* (2006.01)
- *C07C 7/08* (2006.01)
- *C07C 7/11* (2006.01)
- *C07C 2/06* (2006.01)
- *C07C 2/56* (2006.01)
- *C07C 9/16* (2006.01)
- *C07C 11/06* (2006.01)
- *C07C 11/167* (2006.01)

(52) U.S. Cl.
CPC ............... *C07C 2/62* (2013.01); *C07C 6/04* (2013.01); *C07C 7/08* (2013.01); *C07C 7/11* (2013.01); *C07C 9/16* (2013.01); *C07C 11/06* (2013.01); *C07C 11/167* (2013.01); C07C 2521/04 (2013.01); C07C 2523/18 (2013.01); C07C 2523/28 (2013.01); C07C 2523/30 (2013.01); C07C 2523/36 (2013.01); C07C 2523/755 (2013.01); C07C 2527/043 (2013.01); C07C 2527/1206 (2013.01); C07C 2527/126 (2013.01)

(56) References Cited

U.S. PATENT DOCUMENTS

| | | |
|---|---|---|
| 3,932,551 A | 1/1976 | Grasselli et al. |
| 3,956,181 A | 5/1976 | Grasselli et al. |
| 3,959,400 A | 5/1976 | Lucki |
| 3,965,126 A | 6/1976 | Wirth et al. |
| 4,162,234 A | 7/1979 | Grasselli et al. |
| 4,219,388 A | 8/1980 | Heller et al. |
| 4,313,016 A * | 1/1982 | Manning ............... C07C 7/177 585/510 |
| 4,336,409 A | 6/1982 | Yamamoto et al. |
| 4,397,771 A | 8/1983 | Grasselli et al. |
| 4,423,281 A | 12/1983 | Yamamoto et al. |
| 4,424,141 A | 1/1984 | Grasselli et al. |
| 4,504,692 A | 3/1985 | Arakawa et al. |
| 4,511,750 A | 4/1985 | Miller |
| 4,547,615 A | 10/1985 | Yamamoto |
| 4,961,827 A | 10/1990 | Zimmerling et al. |
| 5,324,419 A | 6/1994 | Muldowney |
| 5,849,972 A | 12/1998 | Vicari et al. |
| 6,852,898 B2 | 2/2005 | Schulz et al. |
| 7,259,285 B1 | 8/2007 | Walter et al. |
| 7,932,428 B2 | 4/2011 | Rix et al. |
| 9,255,041 B2 | 2/2016 | Yano et al. |
| 9,399,606 B2 | 7/2016 | Ruttinger et al. |
| 2005/0288471 A1 | 12/2005 | Bitterlich et al. |
| 2007/0191212 A1 | 8/2007 | Schubert et al. |
| 2008/0045766 A1 | 2/2008 | Schubert et al. |
| 2008/0200745 A1 | 8/2008 | Sigl et al. |
| 2009/0030251 A1 | 1/2009 | Senetar et al. |
| 2011/0040134 A1* | 2/2011 | Arnold ............... C07C 5/2506 585/315 |
| 2012/0130137 A1 | 5/2012 | Orita et al. |
| 2013/0281748 A1 | 10/2013 | Cha et al. |
| 2014/0135557 A1* | 5/2014 | Nicholas ............... C10G 50/00 585/653 |
| 2014/0163291 A1 | 6/2014 | Grune et al. |
| 2014/0163292 A1 | 6/2014 | Grune et al. |
| 2014/0200379 A1 | 7/2014 | Josch et al. |
| 2014/0200380 A1 | 7/2014 | Josch et al. |
| 2014/0200381 A1 | 7/2014 | Josch et al. |
| 2014/0163288 A1 | 12/2014 | Ruttinger et al. |
| 2016/0152531 A1 | 6/2016 | Walsdorff et al. |
| 2016/0347686 A1 | 12/2016 | Grune et al. |
| 2016/0355450 A1 | 12/2016 | Grune et al. |
| 2017/0233133 A1 | 8/2017 | Grune et al. |

FOREIGN PATENT DOCUMENTS

| | | |
|---|---|---|
| DE | 2440329 A1 | 3/1975 |
| DE | 2447825 A1 | 8/1975 |
| DE | 2530959 A1 | 2/1976 |
| DE | 2600128 A1 | 7/1976 |
| DE | 4339713 A1 | 5/1995 |
| DE | 102004009803 A1 | 9/2005 |
| DE | 102004009804 A1 | 9/2005 |
| DE | 102004009805 A1 | 9/2005 |
| EP | 272970 A1 | 6/1988 |
| EP | 2711350 A1 | 3/2014 |
| FR | 2641477 A1 | 7/1990 |
| JP | 2011001341 A | 1/2011 |
| JP | 2011006381 A | 1/2011 |
| JP | 2013119530 A | 6/2013 |
| JP | 2013177380 A | 9/2013 |
| KR | 20130036467 A | 4/2013 |
| KR | 20130036468 A | 4/2013 |
| KR | 20130046259 A | 5/2013 |
| WO | WO-9925668 A1 | 5/1999 |
| WO | WO-200137989 A2 | 5/2001 |
| WO | WO-200172670 A1 | 10/2001 |
| WO | WO-2004039757 A2 | 5/2004 |
| WO | WO-2006089956 A2 | 8/2006 |
| WO | WO-2012157495 A1 | 11/2012 |
| WO | WO-2013098760 A1 | 7/2013 |

(56) References Cited

FOREIGN PATENT DOCUMENTS

| WO | WO-2013106039 A1 | 7/2013 |
|----|------------------|--------|
| WO | WO-2014111406 A1 | 7/2014 |
| WO | WO-2014160825 A1 | 10/2014 |

OTHER PUBLICATIONS

Calamur et al. ("Butylenes" Kirk-Othmer Encyclopedia of Chemical Technology, Published Aug. 15, 2003) (Year: 2003).*
U.S. Appl. No. 15/514,077, filed Jul. 5, 2017.
U.S. Appl. No. 15/525,330, filed May 9, 2017.
"Butadien", Ullmann's Encyclopedia of Industrial Chemistry, Band 9, 4. neubearbeitete and erweiterte Auflage, 1975, pp. 1-18.
"Butadiene", Ullmann's Encyclopedia of Industrial Chemistry, 2012, vol. 6, pp. 381-396.
"Butenes", Ullmann's Encyclopedia of Industrial Chemistry, 2014, pp. 1-13.
"Oil Refining", Ullmann's Encyclopedia of Industrial Chemistry, 2000, 6th ed., pp. 1-52.
Albright, L., "Present and Future Alkylation Processes in Refineries", Ind. Eng. Chem. Res., 2009, vol. 48, pp. 1409-1413.
Corma, A., et al., "Chemisty, Catalysts, and Processes for Isoparaffin-Olefin Alkylation: Actual Situation and Future Trends", Catal. Rev.-Sci. Eng., 1993, vol. 35, No. 4, pp. 483-570.
Volkamer, K., et al., "Entwicklungsarbeiten am Butadien—verfahren der BASF", Erdoel und Kohle—Erdgas—Petrochemie, 1981, vol. 34, No. 8, pp. 343-346.
International Prelminary Examination Report for PCT/EP2015/075422 completed Oct. 21, 2016.
International Search Report for PCT/EP2015/075422 dated Jan. 26, 2016.
International Search Report for PCT/EP2015/076018 dated Jan. 25, 2016.
Written Opinion of the International Searching Authority for PCT/EP2015/076018 dated Jan. 26, 2016.

* cited by examiner

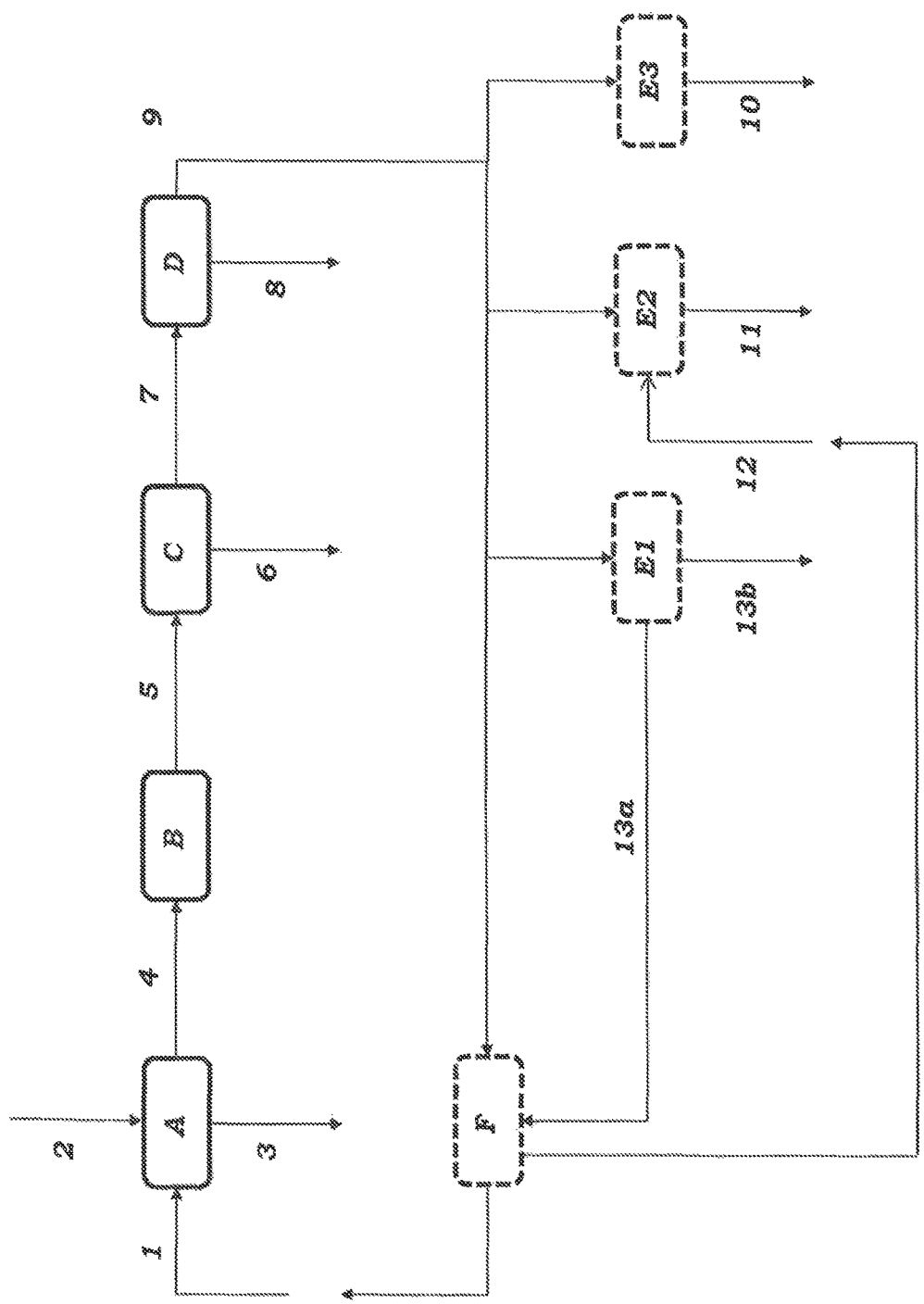

METHOD FOR PRODUCING 1,3-BUTADIENE BY DEHYDROGENATING N-BUTENES, A MATERIAL FLOW CONTAINING BUTANES AND 2-BUTENES BEING PROVIDED

CROSS-REFERENCE TO RELATED APPLICATIONS

This application is a national stage application (under 35 U.S.C. § 371) of PCT/EP2015/076018, filed Nov. 9, 2015, which claims benefit of European Application. No. 14193247.5, filed Nov. 14, 2014, both of which are incorporated herein by reference in their entirety.

The invention relates to a process for preparing 1,3-butadiene by dehydrogenating n-butenes from the C4 product fraction from a fluid catalytic cracking (FCC) plant, with provision of a stream comprising butanes and 2-butenes.

DESCRIPTION OF THE FIGURE

FIG. 1 is a schematic representation of one embodiment of the invention.

DESCRIPTION OF THE INVENTION

Butadiene is an important commodity chemical and is used, for example, for production of synthetic rubbers (butadiene homopolymers, styrene-butadiene rubber or nitrile rubber) or for production of thermoplastic terpolymers (acrylonitrile-butadiene-styrene copolymers). Butadiene is also converted to sulfolane, chloroprene and 1,4-hexamethylenediamine (via 1,4-dichlorobutene and adiponitrile). Through dimerization of butadiene, it is also possible to obtain vinylcyclohexene, which can be dehydrogenated to ethylbenzene or styrene.

1,3-Butadiene can be prepared by thermal cracking of saturated hydrocarbons. A customary process is the steamcracking of naphtha, which affords a hydrocarbon mixture of methane, ethane, ethene, acetylene, propane, propene, propyne, allene, butanes, butenes, butadienes, butynes, methylallene, and C5 and higher hydrocarbons. The proportion of butadiene in the production of a steamcracker depends on the operating conditions ("sharpness") of the cracking stage, but in particular also on the composition of the feed stream. Thus, the yield of 1,3-butadiene tends to be higher when naphtha is used as feed than when low-boiling hydrocarbons are used, whereas virtually no economically relevant amounts of butadiene are obtained in the cracking process when ethane is used as feed. A change in the raw material supply to steamcrackers or a relatively significant rise in demand for butadiene can therefore give rise to a local, regional or global undersupply of butadiene, in which case it is impossible to cover the demand for butadiene from steamcrackers alone.

Increasing significance is therefore being gained by processes for on-purpose preparation of butadiene, for example by dehydrogenation of n-butenes, and the combination of such processes with conventional cracking processes for maximization of the overall butadiene yield.

For example, a process for preparing butadiene by dehydrogenating n-butenes is described in WO 2013/106039. One disadvantage of such non-oxidative processes is generally the significant limitation in conversions resulting from the position of the thermodynamic equilibrium. Often, large amounts of steam are required to shift the equilibrium or to maintain catalyst stability.

1,3-Butadiene can also be obtained by the oxidative dehydrogenation of n-butenes (1-butene and/or 2-butenes). Processes for oxidative dehydrogenation of butenes to butadiene are known in principle.

US 2012/0130137 A1, for example, describes a process of this kind using catalysts comprising oxides of molybdenum, bismuth and generally further metals. For the lasting activity of such catalysts for the oxidative dehydrogenation, a critical minimum level of partial oxygen pressure is required in the gas atmosphere in order to avoid an excessive reduction and hence a loss of performance of the catalysts. For this reason, it is generally also not possible to work with a stoichiometric oxygen input or complete oxygen conversion in the oxydehydrogenation reactor (ODH reactor). US 2012/0130137 A1 describes, for example, an oxygen content of 2.5% to 8% by volume in the output gas.

A significant hurdle for the economically viable introduction of processes for oxidative dehydrogenation of n-butenes to 1,3-butadiene is the chemical engineering complexity, which leads to specific capital and operating costs for the 1,3-butadiene thus prepared. 1,3-Butadiene can be obtained much less expensively by means of extraction from the C4 cut from steamcrackers.

WO 2013/098760 describes a process for increasing the amount of butadiene extractable from a C4 raffinate as obtained in a steamcracker, comprising the steps of:
a) removing 1,3-butadiene from a mixture comprising butanes, butenes and 1,3-butadiene by means of extractive distillation in an extraction unit, giving a so-called raffinate product comprising butanes and butenes;
b) dehydrogenating the raffinate product in the dehydrogenation unit in the presence of a dehydrogenation catalyst and an inert diluent gas, so as to obtain an output stream comprising 1,3-butadiene;
c) recycling the output stream comprising 1,3-butadiene, after removal of the uncondensable constituents, directly into the extraction unit.

A particular disadvantage of the process described in WO2013/098760 is that the quality of the raffinate product leaving the extraction stage is altered by the recycling of the output stream comprising 1,3-butadiene from the dehydrogenation stage into the extraction stage, in that the proportion of those constituents that are converted less efficiently to 1,3-butadiene in the dehydrogenation stage is increased. In many oxidative dehydrogenation processes in the presence of oxygen (ODH), essentially only linear butenes are converted to 1,3-butadiene, while n- and isobutane are substantially inert and isobutene is converted very unselectively with adverse effects on the catalyst performance, and the by-products that form from isobutene, for example methacrolein, can be disruptive in the workup steps.

WO 2014/160825 A1 describes a process very similar to the process described in WO 2013/098760 for increasing the amount of butadiene extractable from a C4 raffinate as obtained in a steamcracker, comprising the steps of:
a) removing 1,3-butadiene from a mixture comprising butanes, butenes and 1,3-butadiene by means of extractive distillation in an extraction unit, giving a first C4 stream comprising butanes and butenes (raffinate product);
b) removing isobutene from the first C4 stream, giving a second C4 stream;
c) dehydrogenating the second C4 stream in the dehydrogenation unit, so as to obtain an output stream comprising 1,3-butadiene;

d) introducing the output stream comprising 1,3-butadiene into an extraction unit or recycling the output stream comprising 1,3-butadiene into the extraction unit mentioned in a).

Removing isobutene means here that the predominant portion of isobutene is removed from the input gas stream a. Typically, more than 60% of isobutenes are removed, preferably more than 80%, more preferably more than 90% and most preferably more than 95%. The ratio of isobutene to n-butenes in stream b is then typically less than 0.2, preferably less than 0.1 and most preferably less than 0.05.

The process described in WO 2014/160825 A1 differs from the process described in WO2013/098760 essentially in that the output stream from the dehydrogenation unit is processed in a complex manner in several stages before being recycled into the extraction unit. More particularly, butane, which is substantially inert in the dehydrogenation unit, is removed before the recycling. The purification is associated with high energy or investment costs.

KR 20130046259 A1 describes a process for using a stream called raffinate 3 from an olefin metathesis as input stream for preparation of 1,3-butadiene by oxidative dehydrogenation of n-butenes. In one embodiment, a crude C4 fraction obtained in a naphtha cracker (steamcracker with naphtha feed) is first run into an extraction stage. This removes the butadiene and gives what is called a raffinate 1. In a further process stage, isobutene is separated from the raffinate 1, giving what is called raffinate 2. This raffinate 2 is subsequently sent to a further process stage (metathesis) in which a portion of the n-butenes removed, with addition of ethylene, is converted to propylene. A butane-rich C4 stream (raffinate 3) leaving the metathesis is finally sent to a further process stage for oxidative dehydrogenation to utilize the remaining n-butenes. The product mixture leaving the oxidative dehydrogenation is separated in various process stages that are not described individually. These give, inter alia, a butadiene and a stream comprising butane and further compounds. The process is unfavorable for the preparation of butadiene, since, on the one hand, a stream having a relatively low content of n-butenes (raffinate 3) is used, whereas, on the other hand, a very extensive workup is required for removal of butadiene. This leads to high specific capital costs.

A fundamental problem with the oxidative dehydrogenation of butenes to 1,3-butadiene is that the selectivity for 1,3-butadiene generally decreases ever further with rising conversion. In the case of conversions greater than 50%, but particularly greater than 80% and especially greater than 90%, the formation of carbon oxides, organic oxygenates or else coke-like products increases to a disproportionate degree, which can lead to increased costs through loss of feedstock, but also to increasing problems in operation or workup. Typically, several butene isomers are present alongside one another in the input stream, and 1-butene is more reactive to many catalyst systems than the 2-butenes, and so 1-butene is converted more quickly than the 2-butenes. The reaction conditions needed for a high conversion of 2-butenes correspondingly promote the subsequent chemical reactions of butadiene, which is formed relatively rapidly from 1-butene, to give unwanted by-products. Various solutions to this problem have already been proposed.

For instance, US 2013/0281748 A1 describes a process for maximizing the yield of 1,3-butadiene, in which 1-butene and the 2-butenes are converted parallel to one another, each in a separate dedicated reactor, to give 1,3-butadiene, utilizing catalysts of different activity. However, this process entails the separation of the isomers and twice the number of reactors. Implementation is therefore made more difficult by high capital costs.

WO 2014/160825 A1 describes a variant of the process already cited above, in which the C4 stream employed is separated into a stream rich in 1-butene and isobutane, and a stream rich in 2-butenes and n-butane. The 1-butene- and isobutane-rich stream is available for another utilization. The stream rich in 2-butenes and n-butane, in contrast, is sent to oxidative dehydrogenation. The output stream from the oxidative dehydrogenation is sent to the extraction unit via various workup stages. In one variant of this process, only a partial conversion of the 2-butenes is achieved, and unconverted 2-butenes in the output stream, after removal of 1,3-butadiene, are recycled into the oxidative dehydrogenation. The 1,3-butadiene removed, in contrast, is recycled via several workup stages into the extraction unit of the cracker from which the C4 stream originally used was withdrawn. This complicated process and variants thereof harbor several disadvantages. For instance, it is unfavorable for the preparation of butadiene, since the stream used consists predominantly of substantially inert butane and the less reactive 2-butenes. In the case of variants of the process with partial conversion of the less reactive 2-butenes, removal and recycling of the unconverted 2-butenes is technically feasible but is associated with high energy or investment costs. At the same time, very extensive workup is required for removal of 1,3-butadiene. One proposed option for processing the previously removed stream of 1-butene and isobutane is the production of polyethylene. For the production of polyethylene, however, 1-butene is used merely as a comonomer, which additionally has to be separated from the isobutane. No favorable further processing option for the removed stream obtained is described in WO 2014/160825 A1.

U.S. Pat. No. 4,504,692 describes a process for oxidative dehydrogenation of butenes from a C4 stream which has been freed of isobutene, in which unconverted n-butenes are returned to the dehydrogenation and butanes are removed in return, such that two output streams essentially comprising butadiene and essentially comprising butanes are obtained. However, such a splitting of butanes and butenes is demanding in apparatus terms and energy-intensive.

In general, in processes which include the removal of a substream, the question of the most valuable possible utilization of the streams obtained arises. The same applies to processes having partial conversion, in which costly and inconvenient recycling of the butenes is dispensed with. In this case, the aim is the most valuable possible utilization of a C4 stream which comprises butenes and is obtained after the removal of 1,3-butadiene.

It was therefore also an object of the present invention to provide a process in which, as well as a stream comprising 1,3-butadiene, a stream which comprises butenes and can be processed further in the most valuable manner possible is provided and is processed further in the most valuable manner possible, in order to make the economic viability of the process as favorable as possible overall through minimum investment or energy costs.

WO 2004/039757 describes a process for preparing butene oligomers. This uses a C4 hydrocarbon stream from an FCC plant which has been freed of butadiene and comprises butenes and butanes. No dehydrogenation is described.

WO 2006/089956 describes a process for preparing ethene or propene by olefin metathesis of a C4 hydrocarbon input stream. The C4 input stream can be obtained from a C4 hydrocarbon stream from an FCC plant, by virtually freeing it of butadiene by extractive distillation, giving a raffinate I comprising 0% to 5% by weight of 1-butene. However, an extractive distillation for removal of butadiene is unviable without prior enrichment of butadiene for typical streams from an FCC plant (<1% by weight of butadiene).

U.S. Pat. No. 5,324,419 describes a process for operating an FCC plant for minimization of the butadiene yield in the C4 cut, since the butadiene content in the C4 product cut from an FCC plant is generally too low for economically viable extractability. However, butadiene is troublesome in most subsequent steps, and it is therefore regularly removed by selective hydrogenation. Since hydrogen is consumed for this purpose, it may be advisable to keep butadiene formation as low as possible in the FCC plant.

US 2009/0030251 A1 describes a process for preparing alkylates from saturated and olefinic C4 by-products from a cracker. The C4 hydrocarbon input streams may originate from an FCC plant, in which case the streams are essentially freed of 1,3-butadiene by hydrogenation and the ratio of 2-butene to 1-butene is increased by isomerizing 1-butene to 2-butene.

Processes for alkylation of isobutane and n-butenes, as processes of significance in refineries, are also described by Corma and Martinez (Catal. Rev.—Sci. Eng., 35(4). 483-570, 1993) and by Albright (Ind. Eng. Chem. Res. 2009, 48, 1409-1413). It becomes clear in this context that, especially when sulfuric acid is used as catalyst, more favorable product compositions can be obtained when using 2-butenes compared to 1-butene.

CN 101492334 B describes a process for preparing propylene from a C4 hydrocarbon input stream by olefin metathesis. The C4 hydrocarbon input stream may originate from an FCC plant, in which case the stream is essentially freed of 1,3-butadiene by hydrogenation and the ratio of 2-butenes to 1-butene is increased by isomerizing 1-butene to 2-butene. In addition, isobutene is removed by distillation.

CN 101492335 B describes a process for preparing propylene from a C4 hydrocarbon input stream by olefin metathesis. The C4 hydrocarbon input stream may originate from an FCC plant, in which case the stream is freed of butadiene by extractive distillation and the ratio of 2-butene to 1-butene is increased by isomerization. However, an extractive distillation for removal of butadiene from typical FCC plant streams (<1% by weight of butadiene) without prior enrichment of butadiene is costly and inconvenient and not very economically attractive.

It is thus an object of the invention to provide a process which is advantageous overall for preparation of 1,3-butadiene by dehydrogenating n-butenes from an FCC plant, in which the hydrocarbons present in the input gas stream from the dehydrogenation are utilized physically in an optimal manner.

The object is achieved by a process for preparing 1,3-butadiene from n-butenes, comprising the steps of:
A) providing an input gas stream a comprising butanes, 1-butene, 2-butene and isobutene, with or without 1,3-butadiene, from an FCC plant; in a preferred variant of the process, the provision can be effected by means of a unit for selective hydrogenation, which serves, for example, for conversion of alkynes to olefins or for conversion of diolefins to olefins;
B) removing isobutene from the input gas stream a, giving a stream b comprising butanes, 1-butene and 2-butenes, with or without 1,3-butadiene;
C) feeding the stream b comprising butanes, 1-butene and 2-butene and optionally an oxygenous gas and optionally water vapor into at least one dehydrogenating zone and dehydrogenating 1-butene and 2-butene to 1,3-butadiene, giving a product gas stream c comprising 1,3-butadiene, butanes, 2-butene and water vapor, with or without oxygen, with low-boiling hydrocarbons, with high-boiling secondary components, with or without carbon oxides and with or without inert gases;
D) cooling and compressing the product gas stream c, giving at least one aqueous condensate stream d1 and a gas stream d2 comprising 1,3-butadiene, butanes, 2-butenes and water vapor, with or without oxygen, with low-boiling hydrocarbons, with or without carbon oxides and with or without inert gases;
Ea) removing uncondensable and low-boiling gas constituents comprising low-boiling hydrocarbons, with or without oxygen, with or without carbon oxides and with or without inert gases, as gas stream e2 from the gas stream d2 by absorbing the C4 hydrocarbons comprising 1,3-butadiene, butanes and 2-butenes in an absorbent, giving an absorbent stream laden with C4 hydrocarbons and the gas stream e2, and
Eb) subsequently desorbing the C4 hydrocarbons from the laden absorbent stream, giving a C4 hydrocarbon stream e1;
F) separating the C4 hydrocarbon stream e1 by extractive distillation with a 1,3-butadiene-selective solvent into a stream f1 comprising 1,3-butadiene and the selective solvent and a stream f2 comprising butanes and 2-butenes;
wherein
at least 90%, preferably at least 95% and especially preferably at least 99% of the 1-butene present in stream b is converted in step C), and product stream comprising butanes and 2-butenes is provided in step F.

In a preferred embodiment, the stream f2 which comprises butanes and 2-butene and is obtained in step F) is converted further in one or more of steps G1), G2) or G3) by
G1) alkylating 2-butenes with butanes to give isooctanes;
G2) subjecting 2-butenes to olefin metathesis with ethene to give propene;
G3) oligomerizing 2-butene.

The stream f2 obtained may optionally also be pretreated for any of the possible steps G1), G2) or G3). For example, butadiene which may still be present in small amounts can be removed, for example, by selective hydrogenation.

According to the invention, a $C_4$ hydrocarbon stream which has been freed of isobutene from an FCC plant, comprising butanes and n-butenes (1-butene and 2-butene), with or without small amounts of 1,3-butadiene, is sent to a dehydrogenation stage.

The $C_4$ cut separated from the product gas mixture from the dehydrogenation stage (predominantly butanes, 1,3-butadiene and 2-butene) is sent to a butadiene extraction, and so the remaining stream comprises essentially butanes (n-butane and isobutane) and 2-butene (cis- and trans-2-butene). The dehydrogenation stage may, especially in the case of an oxidative dehydrogenation, be conducted in such a way that 1-butene is converted virtually quantitatively, but unconverted 2-butene remains in the product gas stream from the dehydrogenation. Stages C), D), E) and F) of the process according to the invention can be conducted in a typical refinery infrastructure, the hydroisomerization unit for enrichment of 2-butenes relative to 1-butene and the unit for removal of oxygenates. A hydrogenation unit can be provided in order to provide a suitable input gas stream for the dehydrogenation, for example in order to remove acetylenes, alkynes or 1,2-butadiene. Butanes are substantially inert in the dehydrogenation stage. Oxygenates, for example formaldehyde, formic acid, acetaldehyde, acetic acid, acrolein, acrylic acid, propionaldehyde, propionic acid, methacrolein, methacrylic acid, crotonaldehyde, crotonic acid, methyl vinyl ketone, furan, maleic anhydride, styrene, benzaldehyde, benzoic acid, phthalic anhydride, fluorenone, anthraquinone and butyraldehyde, are removed in the process according to the invention in stages D), E) and F) in particular.

Should the separation performance for oxygenates be inadequate, or should an even higher separating performance be advantageous for the continuation of the process, particularly for steps G1), G2) and G3), it is possible in a preferred variant for further process steps which further reduce the concentration of the oxygenates in stream f2 to be conducted after stage C) or later stages.

Thus, the process according to the invention achieves the following advantages:
(i) a portion of the C4 hydrocarbon mixture that originates from the FCC plant is upgraded to 1,3-butadiene;
(ii) the dehydrogenation stage can be conducted within a range with relatively low butene conversions and relatively high selectivities, with provision not only of butadiene but of a further output stream comprising essentially 2-butenes and butanes, which can be utilized in a very valuable manner especially also with regard to the 2-butenes present therein, without needing to remove them or hydrogenate them out;
(iii) the $C_4$ hydrocarbon stream f2 that remains after removal of 1,3-butadiene by extractive distillation is high in 2-butene and butanes and low in 1-butene. It is suitable for high-value utilization, especially for a further conversion
a. by alkylating 2-butene with butanes to give isooctanes,
b. by olefin metathesis with ethylene to give propylene,
c. by oligomerization to give butene oligomers, especially to give $C_8$ and $C_{12}$ olefins; these can optionally be recycled back into the FCC plant.

In a stage A), an input gas stream a comprising n-butenes and isobutene, with or without small amounts of 1,3-butadiene, from an FCC plant is provided. In a preferred variant, any small proportion of 1,3-butadiene present and any dienes or alkynes also present in small proportions are removed by selective dehydrogenation.

Typically, the C4 product fraction from an FCC plant provided as input gas stream a, according to the "cracking severity", comprises about 0.2% to 1.0% by volume of 1,3-butadiene, about 10% to 20% by volume of 1-butene, 10% to 30% by volume of 2-butene (cis- and trans-2-butene), about 15% to 25% by volume of isobutene, 5% to 15% by volume of n-butane and 25% to 40% by volume of isobutane.

TABLE 1

Typical composition of components (in wt %) of C4 product fractions from an FCC plant with moderate "cracking severity" according to Ullmann's Encyclopedia of Industrial Chemistry, Published Online: 31 Jan. 2014 Butene

| Component | FCC | Steamcracker |
|---|---|---|
| isobutane | 37 | 2 |
| n-butane | 13 | 6 |
| isobutene | 15 | 26 |
| 1-butene | 12 | 14 |
| trans-2-butene | 12 | 5 |

TABLE 1-continued

Typical composition of components (in wt %) of C4 product fractions from an FCC plant with moderate "cracking severity" according to Ullmann's Encyclopedia of Industrial Chemistry, Published Online: 31 Jan. 2014 Butene

| Component | FCC | Steamcracker |
|---|---|---|
| cis-2-butene | 11 | 4 |
| 1,3-butadiene | <0.5 | 43 |

The $C_4$ product fraction from an FCC plant is notable for a low proportion of 1,3-butadiene and high proportions of 1-butene, 2-butene and butanes. In contrast, the C4 product fraction from a naphtha steamcracker typically comprises a high proportion of 1,3-butadiene (up to about 50% by volume) but only small amounts of isobutane.

In the known FCC process (cf. Ullmann's Encyclopedia of Industrial Chemistry, Wiley-VCH Verlag GmbH, Weinheim, Germany, Sixth Edition, 2000 Electronic Release, Chapter Oil Refining, 3.2. Catalytic Cracking), the corresponding hydrocarbon is evaporated and contacted in a short-contact reactor—called the "riser"—in the gas phase with a pulverulent heterogeneous catalyst at a temperature of 450 to 500° C. Typically, an FCC unit is supplied with a fraction having an average molar mass of about 200 to about 600 g mol and a boiling range from about 340° C. to about 560° C. Suitable fractions therefore appear to be heavy gas oil, vacuum gas oil (VGO), deasphalted oil (DAO) or furfural extract. The catalyst particles are transported along the riser by the hydrocarbon stream and then pass into the cycle portion of the FCC plant. The pulverulent catalyst is separated therein from the gaseous product stream of the process and fed to the regeneration section of the FCC plant.

Various product streams are obtained in several workup steps from the crude product stream of the FCC process. In the main product removal section (main fractionator), the slurry oil and the heavy oil (fuel oil) and higher-boiling by-products (side products), for example heavy naphtha and light cycle oil, are first separated from the crude product stream in a distillation column. The remaining product stream is then transferred into a condensation section (GCU=gas concentration unit), and the FCC crude gasoline (overhead liquid) is liquefied therein. This stream is finally separated in the liquid gas removal into the FCC gasoline (cracked naphtha), the liquefied gas fraction (LPG=liquefied petroleum gas) and the remaining FCC residual gas (fuel gas). The liquefied gas fraction comprises the C4 hydrocarbons that are of interest here, and also C3 hydrocarbons. The latter are usually separated from the C4 fraction in a further plant section—called the propylene recovery unit—which ultimately gives the FCC C4 fraction.

Catalysts used for the FCC process are typically synthetic crystalline zeolites, with catalytic cracking of the hydrocarbon molecules of the feedstock of the acidic sites thereof.

In a step B), isobutene is separated from the input gas stream a, giving a stream b comprising butanes and n-butenes. The separation is generally effected by derivatizing isobutene and then removing the derivative by a thermal separation process. Preferably, isobutene is derivatized with methanol to give methyl tert-butyl ether (MTBE) or with ethanol to give ethyl tert-butyl ether (ETBE), and the derivative is then removed by distillation. Processes of this kind are known in principle to those skilled in the art and are described, for example, in U.S. Pat. No. 7,932,428 B2. The derivatization, for example by etherification to give MTBE or ETBE, and distillative removal of the derivative can be conducted, for example, in a combined process step in a reactive distillation column.

In a step C), the stream b comprising butanes and n-butenes and optionally an oxygenous gas and optionally water vapor are fed into at least one dehydrogenation zone and the n-butenes are dehydrogenated to 1,3-butadiene, giving a product gas stream c comprising 1,3-butadiene, butanes, unconverted n-butenes, especially 2-butene, and water vapor, with or without oxygen, with low-boiling hydrocarbons, with high-boiling secondary components, with or without carbon oxides and with or without inert gases. Step C) is conducted such that the 1-butene present in the stream b is converted to an extent of at least 90%, preferably at least 95% and especially preferably at least 99%.

Step C) can be conducted as a nonoxidative dehydrogenation. In this case, the stream b comprising butanes and n-butenes and water vapor are fed into the at least one dehydrogenation zone and n-butenes are dehydrogenated to 1,3-butadiene, giving a product gas stream c comprising 1,3-butadiene, unconverted n-butenes, especially 2-butene, water vapor, low-boiling hydrocarbons and high-boiling secondary components.

Preferably, step C) is conducted as an oxidative dehydrogenation (oxydehydrogenation, ODH). In this case, the stream b comprising butanes and n-butenes and an oxygenous gas are fed into the at least one dehydrogenation zone and n-butenes are dehydrogenated to 1,3-butadiene, giving a product gas stream c comprising 1,3-butadiene, butanes, unconverted n-butenes, especially 2-butene, water vapor, oxygen, low-boiling hydrocarbons and high-boiling secondary components, with or without carbon oxides and with or without inert gases.

Catalysts suitable for the oxydehydrogenation are generally based on an Mo—Bi—O-containing multimetal oxide system which generally additionally comprises iron. In general, the catalyst system also comprises further additional components, for example potassium, cesium, magnesium, zirconium, chromium, nickel, cobalt, cadmium, tin, lead, germanium, lanthanum, manganese, tungsten, phosphorus, cerium, aluminum or silicon. Iron-containing ferrites have also been proposed as catalysts.

In a preferred embodiment, the multimetal oxide comprises cobalt and/or nickel. In a further preferred embodiment, the multimetal oxide comprises chromium. In a further preferred embodiment, the multimetal oxide comprises manganese.

Examples of Mo—Bi—Fe—O-containing multimetal oxides are Mo—Bi—Fe—Cr—O- or Mo—Bi—Fe—Zr—O-containing multimetal oxides. Preferred systems are described, for example, in U.S. Pat. No. 4,547,615 ($Mo_{12}BiFe_{0.1}Ni_8ZrCr_3K_{0.2}O_x$ and $Mo_{12}BiFe_{0.1}Ni_8AlCr_3K_{0.2}O_x$), U.S. Pat. No. 4,424,141 ($Mo_{12}BiFe_3Co_{4.5}Ni_{2.5}P_{0.5}K_{0.1}O_x+SiO_2$), DE-A 25 30 959 ($Mo_{12}BiFe_3Co_{4.5}Ni_{2.5}Cr_{0.5}K_{0.1}O_x$, $Mo_{13.75}BiFe_3Co_{4.5}Ni_{2.5}Ge_{0.5}K_{0.8}O_x$, $Mo_{12}BiFe_3Co_{4.5}Ni_{2.5}Mn_{0.5}K_{0.1}O_x$ and $Mo_{12}BiFe_3Co_{4.5}Ni_{2.5}La_{0.5}K_{0.1}O_x$), U.S. Pat. No. 3,911,039 ($Mo_{12}BiFe_3Co_{4.5}Ni_{2.5}Sn_{0.5}K_{0.1}O_x$), DE-A 25 30 959 and DE-A 24 47 825 ($Mo_{12}BiFe_3Co_{4.5}Ni_{2.5}W_{0.5}K_{0.1}O_x$).

Suitable multimetal oxides and the preparation thereof are additionally described in U.S. Pat. No. 4,423,281 ($Mo_{12}BiNi_8Pb_{0.5}Cr_3K_{0.2}O_x$ and $Mo_{12}Bi_bNi_7Al_3Cr_{0.5}K_{0.5}O_x$), U.S. Pat. No. 4,336,409 ($Mo_{12}BiNi_6Cd_2Cr_3P_{0.5}O_x$), DE-A 26 00 128 ($Mo_{12}BiNi_{0.5}Cr_3P_{0.5}Mg_{7.5}K_{0.1}O_x$ $SiO_2$) and DE-A 24 40 329 ($Mo_{12}BiCo_{4.5}Ni_{2.5}Cr_3P_{0.5}K_{0.1}O_x$).

Particularly preferred catalytically active multimetal oxides comprising molybdenum and at least one further metal have the general formula (Ia):

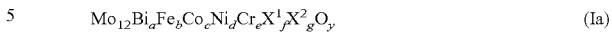

with
$X^1$=Si, Mn and/or Al,
$X^2$=Li, Na, K, Cs and/or Rb,
$0.2 \leq a \leq 1$,
$0.5 \leq b \leq 10$,
$0 \leq c \leq 10$,
$0 \leq d \leq 10$,
$2 \leq c+d \leq 10$
$0 \leq e \leq 2$,
$0 \leq f \leq 10$,
$0 \leq g \leq 0.5$,
y=a number which, with the prerequisite of charge neutrality, is determined by the valency and frequency of the elements in (Ia) other than oxygen.

Preference is given to catalysts whose catalytically active oxide composition, of the two metals Co and Ni, has only Co (d=0). Preferred is $X^1$ Si and/or Mn and $X^2$ is preferably K, Na and/or Cs, more preferably $X^2$=K. Particular preference is given to a substantially Cr(VI)-free catalyst.

Very particular preference is given to conducting oxidative dehydrogenations using catalysts comprising oxides of bismuth and molybdenum, as described, for example, in US 2012/0130137A1. They are particularly suitable for establishing a virtually full conversion of 1-butene, in addition to a partial conversion of 2-butenes. One possible source of the C4 gas stream mentioned in US2012/0130137A1 is an FCC cracker.

For performance of the oxidative dehydrogenation (ODH) at high total conversion of n-butenes, preference is given to a gas mixture having a molar oxygen:n-butenes ratio of at least 0.5. Preference is given to working at an oxygen:n-butenes ratio of 0.55 to 10. To set this value, the output gas can be mixed with oxygen or an oxygenous gas and optionally additional inert gas, methane or steam. The oxygenous gas mixture obtained is then fed to the oxydehydrogenation.

The reaction temperature in the oxydehydrogenation is generally controlled by a heat exchange medium present around the reaction tubes. Examples of useful liquid heat exchange media of this kind include melts of salts or salt mixtures such as potassium nitrate, potassium nitrite, sodium nitrite and/or sodium nitrate, and melts of metals such as sodium, mercury and alloys of various metals. It is also possible to use ionic liquids or heat carrier oils. The temperature of the heat exchange medium is between 220 to 490° C. and preferably between 300 to 450° C. and more preferably between 350 and 420° C.

Because of the exothermicity of the reactions which proceed, the temperature in particular sections of the reaction interior during the reaction may be higher than that of the heat exchange medium, and what is called a hotspot develops. The position and magnitude of the hotspot is decided by the reaction conditions, but it can also be regulated through the dilution ratio of the catalyst layer or the flow rate of mixed gas. The difference between hotspot temperature and the temperature of the heat exchange medium is generally between 1-150° C., preferably between 10-100° C. and more preferably between 20-80° C. The temperature at the end of the catalyst bed is generally between 0-100° C., preferably between 0.1-50° C., more preferably between 1-25° C., above the temperature of the heat exchange medium.

The oxydehydrogenation can be performed in all fixed bed reactors known from the prior art, for example in a staged oven, in a fixed bed tubular reactor or shell and tube reactor, or in a plate heat exchanger reactor. A shell and tube reactor is preferred.

If individual tubes are to be equipped with thermal tubes, the pressure drop over these tubes is preferably adjusted such that it corresponds substantially to that of the other tubes.

Preferably, the oxidative dehydrogenation is performed in fixed bed tubular reactors or fixed bed shell and tube reactors. The reaction tubes (just like the other elements of the shell and tube reactor) are generally manufactured from steel. The wall thickness of the reaction tubes is typically 1 to 3 mm. The internal diameter thereof is generally (uniformly) 10 to 50 mm or 15 to 40 mm, frequently 20 to 30 mm. The number of reaction tubes accommodated in a shell and tube reactor generally runs to at least 1000, or 3000, or 5000, preferably to at least 10 000. Frequently, the number of reaction tubes accommodated in a shell and tube reactor is 15 000 to 30 000, or to 40 000 or to 50 000. The length of the reaction tubes normally extends to a few meters, a typical reaction tube length being in the range from 1 to 8 m, frequently 2 to 7 m, in many cases 2.5 to 6 m.

In addition, the catalyst layer set up in the ODH reactor may consist of a single layer or of 2 or more layers. These layers may consist of a pure catalyst or be diluted with a material which does not react with the output gas or components from the product gas of the reaction. In addition, the catalyst layers may consist of unsupported material and/or supported eggshell catalysts.

For many catalyst systems, 1-butenes are more reactive than 2-butenes, and so they react preferentially under given conditions in the reactor before 2-butenes are converted fully. Under given reaction conditions, the overall conversion of butenes is thus dependent on the exact ratio of 1- to 2-butenes. The overall conversion of butenes in an industrial process can be adjusted by the person skilled in the art on the basis of experimental results with a particular catalyst and optionally with corresponding modeling. A particular target conversion can be established by means of various manipulated variables, for example salt bath temperature, diameter and length of the reactor tubes and length and volume of the catalyst beds, optionally dilution of the catalysts with inert material or space velocity of feed stream through the reactors, etc. In the case of a conversion of total butenes of at least 48% percentage points above the proportion of 1-butene in the butenes, it is regularly possible to assume a virtually full conversion of 1-butene (greater than 98%). It is also possible to exert control by a corresponding analysis of the reactor output stream.

The product gas stream c leaving the oxidative dehydrogenation comprises, as well as butadiene, generally also butanes and unconverted n-butenes, oxygen and water vapor. According to the invention, 1-butene is converted almost completely and 2-butene only incompletely. As further components, stream c generally comprises carbon monoxide, carbon dioxide and inert gases (principally nitrogen), with or without low-boiling hydrocarbons such as methane, ethane, ethene, propane and propene, butane and isobutane, and with oxygen-containing hydrocarbons, called oxygenates. Oxygenates may, for example, be formaldehyde, furan, acetic acid, maleic anhydride, formic acid, methacrolein, methacrylic acid, crotonaldehyde, crotonic acid, propionic acid, acrylic acid, methyl vinyl ketone, styrene, benzaldehyde, benzoic acid, phthalic anhydride, fluorenone, anthraquinone and butyraldehyde.

In general, the product gas stream c still comprises not more than 10%, preferably not more than 5%, especially less than 1%, of the 1-butene present in the charge gas mixture of the oxydehydrogenation (stream b). In general, the product gas stream c still comprises at least 10%, preferably at least 15%, of the 2-butene present in the charge gas mixture of the oxydehydrogenation (stream b). In a step D), the product gas stream c is cooled and compressed, giving at least one aqueous condensate stream d1 and a gas stream d2 comprising 1,3-butadiene, butanes, n-butenes, water vapor, oxygen and low-boiling hydrocarbons, with or without carbon oxides and with or without inert gases.

In general, step D) comprises the steps of:

Da) cooling the product gas stream c by contacting it with a coolant and condensing at least a portion of the high-boiling secondary components;

Db) compressing the remaining product gas stream c in at least one compression stage, giving at least one aqueous condensate stream d1 and one gas stream d2 comprising 1,3-butadiene, butanes, n-butenes, water vapor, oxygen and low-boiling hydrocarbons, with or without carbon oxides and with or without inert gases.

In general, an aqueous coolant or an organic solvent is used in the cooling stage Da).

Preference is given to using an organic solvent in the cooling stage Da). These organic solvents generally have a very much higher dissolution capacity for the high-boiling by-products which can lead to deposits and blockages in the plant parts downstream of the ODH reactor than water or aqueous alkaline solutions. Organic solvents used with preference as coolants are aromatic hydrocarbons, for example toluene, o-xylene, m-xylene, p-xylene, diethylbenzenes, triethylbenzenes, diisopropylbenzenes, triisopropylbenzenes and mesitylene or mixtures thereof. Particular preference is given to mesitylene.

Embodiments which follow are preferred or particularly preferred variants of the process according to the invention:

Stage Da) is performed in multiple stages in stages Da1) to Dan), preferably in two stages in two stages Da1) and Da2). In this case, particular preference is given to feeding at least a portion of the solvent as coolant to the first stage Da1) after it has passed through the second stage Da2).

Stage Db) generally comprises at least one compression stage Dba) and at least one cooling stage Dbb). Preferably, in the at least one cooling stage Dbb), the gas compressed in the compression stage Dba) is contacted with a coolant. More preferably, the coolant in the cooling stage Dbb) comprises the same organic solvent which is used as a coolant in stage Da). In an especially preferred variant, at least some of this coolant is fed as a coolant to stage Da) after it has passed through the at least one cooling stage Dbb).

Preferably, stage Db) comprises a plurality of compression stages Dba1) to Dban) and cooling stages Dbb1) to Dbbn), for example four compression stages Dba1) to Dba4) and four cooling stages Dbb1) to Dbb4).

Subsequently, in an absorption step Ea), the uncondensable and low-boiling gas constituents comprising low-boiling hydrocarbons, with or without oxygen, with or without carbon oxides and with or without inert gases, are separated as gas stream e2 from the gas stream d2 by absorbing the $C_4$ hydrocarbons comprising 1,3-butadiene, butanes and n-butenes in an absorbent, giving an absorbent stream laden with $C_4$ hydrocarbons and the gas stream e2, and then the $C_4$ hydrocarbons are desorbed from the laden absorbent stream in a subsequent desorption step Eb), giving a $C_4$ hydrocarbon stream e1.

The oxygenous gas stream e2 is recycled into the oxidative dehydrogenation as circulation stream, generally after removal of a purge gas stream. The purge stream is generally sent to an offgas treatment and can be incinerated, for example, in a flare, by catalytic postcombustion or in a process burner.

The gas stream e2 can also be sent to an offgas treatment. Preferably, step Ea) comprises steps Ea1), Ea2) and Eb):

Ea1) absorbing the C4 hydrocarbons comprising 1,3-butadiene, n-butenes and butanes in a high-boiling absorbent, giving an absorbent stream laden with C4 hydrocarbons and the gas stream f2, Ea2) removing oxygen from the absorbent stream laden with C4 hydrocarbons from step Ea1) by stripping with an uncondensable gas stream, and Eb) desorbing the C4 hydrocarbons from the laden absorbent stream, giving a C4 hydrocarbon stream f1 consisting essentially of C4 hydrocarbons and comprising less than 100 ppm of oxygen.

In a preferred embodiment, the high-boiling absorbent used in step Ea) is an aromatic hydrocarbon solvent, more preferably the aromatic hydrocarbon solvent used in step Da), especially mesitylene. It is also possible to use diethylbenzenes, triethylbenzenes, diisopropylbenzenes and triisopropylbenzenes.

The absorption stage can be conducted in any desired suitable absorption column known to those skilled in the art. The absorption can be effected by simply passing the product gas stream d2 through the absorbent. However, it can also be effected in columns or in rotary absorbers. It is possible to work in cocurrent, countercurrent or crosscurrent. The absorption is preferably conducted in countercurrent. Suitable absorption columns are, for example, tray columns having bubble-cap, centrifugal and/or sieve trays, columns having structured packings, for example sheet metal packings having a specific surface area of 100 to 1000 $m^2/m^3$, such as Mellapak® 250 Y, and columns having random packings. Also useful, however, are trickle towers and spray towers, graphite block absorbers, surface absorbers such as thick-layer and thin-layer absorbers, and also rotary columns, pan scrubbers, cross-spray scrubbers and rotary scrubbers.

In one embodiment, the gas stream d2 comprising 1,3-butadiene, butanes, n-butenes and the low-boiling and uncondensable gas constituents is supplied to an absorption column in the lower region. In the upper region of the absorption column, the high-boiling absorbent is applied.

Inert absorption media used in the absorption stage are generally high-boiling nonpolar solvents in which the $C_4$ hydrocarbon mixture to be separated off has a significantly higher solubility than the remaining gas components to be separated off. Suitable absorbents are comparatively nonpolar organic solvents, for example aliphatic $C_8$- to $C_{18}$-alkanes, or aromatic hydrocarbons such as the middle oil fractions from paraffin distillation, toluene or ethers having bulky groups, or mixtures of these solvents, to which a polar solvent such as dimethyl 1,2-phthalate may be added. Suitable absorbents are additionally esters of benzoic acid and phthalic acid with straight-chain $C_1$-$C_8$-alkanols, and what are called heat carrier oils, such as biphenyl and diphenyl ethers, chlorine derivatives thereof and triarylalkenes. A suitable absorbent is a mixture of biphenyl and diphenyl ether, preferably in the azeotropic composition, for example the commercially available Diphyl®. Frequently, this solvent mixture comprises dimethyl phthalate in an amount of 0.1% to 25% by weight.

In a preferred embodiment, the same solvent is used in the absorption stage Ea1) as in the cooling stage Da).

Preferred absorbents are solvents having a dissolution capacity for organic peroxides of at least 1000 ppm (mg of active oxygen/kg of solvent). Preference is given to aromatic hydrocarbons, particular preference to toluene, o-xylene, p-xylene and mesitylene, or mixtures thereof. It is also possible to use diethylbenzene, triethylbenzene, diisopropylbenzene and triisopropylbenzene.

At the top of the absorption column, a gas stream e2 is drawn off, comprising essentially oxygen and low-boiling hydrocarbons (methane, ethane, ethene, propane, propene), with or without $C_4$ hydrocarbons (butane, butenes, 1,3-butadiene), with or without inert gases, with or without carbon oxides and with or without water vapor.

At the bottom of the absorption column, in a further column, by purging with a gas, it is possible to discharge residues of oxygen dissolved in the absorbent. The remaining oxygen content is preferably sufficiently small be that the stream which comprises butane, butenes and 1,3-butadiene leaving the desorption column comprises only a maximum of 100 ppm of oxygen. The restriction of the oxygen content prevents the formation of peroxides and of voluminous polymers ("popcorn").

The stripping of the oxygen in step Eb) can be performed in any desired suitable column known to those skilled in the art. The stripping can be effected by simply passing uncondensable gases, preferably gases that are absorbable only slightly, if at all, in the absorbent stream, such as methane, through the laden absorption solution. $C_4$ hydrocarbon additionally stripped out is washed back into the absorption solution in the upper portion of the column, by passing the gas stream back into this absorption column. This can be effected either by means of pipe connection of the stripper column or direct mounting of the stripper column below the absorber column. This direct coupling can be effected since the pressure in the stripping column section and absorption column section is the same. Suitable stripping columns are, for example, tray columns having bubble-cap, centrifugal and/or sieve trays, columns having structured packings, for example sheet metal packings having a specific surface area of 100 to 1000 $m^2/m^3$, such as Mellapak® 250 Y, and columns having random packings. Also useful, however, are trickle towers and spray towers, and also rotary columns, pan scrubbers, cross-spray scrubbers and rotary scrubbers. Suitable gases are, for example, nitrogen or methane.

In step F), the C4 hydrocarbon stream e1 is separated by extractive distillation with a butadiene-selective solvent into a stream f1 comprising 1,3-butadiene and the selective solvent and a stream f2 comprising butanes and 2-butene.

The extractive distillation can be performed, for example, as described in "Erdöl und Kohle-Erdgas-Petrochemie", volume 34 (8), pages 343 to 346, or "Ullmanns Enzyklopädie der Technischen Chemie", volume 9, 4th edition 1975, pages 1 to 18. For this purpose, the $C_4$ product gas stream is contacted with an extractant, preferably an N-methylpyrrolidone (NMP)/water mixture, in an extraction zone. The extraction zone generally takes the form of a scrubbing column comprising trays, random packings or structured packings as internals. This generally has 30 to 70 theoretical plates, in order that a sufficiently good separating action is achieved. Preferably, the scrubbing column has a re-scrubbing zone in the top of the column. This re-scrubbing zone serves for recovery of the extractant present in the gas phase with the aid of a liquid hydrocarbon return stream, for which the top fraction is condensed beforehand. The mass ratio of extractant to $C_4$ product gas stream in the feed to the extraction zone is generally 10:1 to 20:1. The extractive distillation is preferably operated at a bottom temperature in the range from 100 to 250° C., especially at a temperature in the range from 110 to 210° C., a top temperature in the range from 10 to 100° C., especially in the range from 20 to 70° C., and a pressure in the range from 1 to 15 bar, especially in the range from 3 to 8 bar. The extractive distillation column has preferably 5 to 70 theoretical plates.

The stream f2 comprising butanes and 2-butene generally comprises principally butanes (iso- or n-butane). The n-butenes present are generally, particularly when the preceding dehydrogenation has been executed as an oxydehydrogenation, principally cis- or trans-2-butene with only small amounts of 1-butene. Stream f2 thus differs from stream b in the process according to the invention by a distinctly higher proportion of butenes and a distinctly higher proportion of 2-butene compared to 1-butene. The n-butenes present in stream f2 are generally very predominantly 2-butenes. Any relatively small amounts of isobutene that have not been completely removed and are still present in stream b are converted in a substantially unselective manner in the oxydehydrogenation.

Stream f2 is typically obtained with a pressure level of 4-6 bar. This pressure level corresponds to typical pressures in the case of a $H_2SO_4$-catalyzed alkylation to isooctane. In the case of an HF-catalyzed alkylation, a pressure level of 8-20 bar is customary.

The stream #1 obtained at the bottom of the extractive distillation column generally comprises the extractant, 1,3-butadiene and small proportions of 2-butene and butanes.

According to the invention, stream f2 is converted further in one or more of steps G1), G2) or G3) by
G1) alkylating 2-butene with butanes to give isooctanes;
G2) subjecting 2-butene to olefin metathesis with ethene to give propene;
G3) oligomerizing 2-butene.

Stream f2 and optionally further butanes are fed into the alkylation stage G1). The alkylation is generally conducted at temperatures of 40 to 120° C. and pressures of 3.5 bar and 42 bar. Suitable alkylation catalysts comprise sulfuric acid and hydrofluoric acid, and also solid acids such as chlorinated alumina, aluminosilicates and aluminophosphates.

A mixture of isooctanes (called gasoline alkylate) is obtained.

The underlying chemistry can be described in simplified formed by two partial reaction equations:

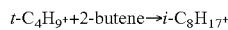
$t\text{-}C_4H_9{}^+ + 2\text{-butene} \rightarrow i\text{-}C_8H_{17}{}^+$

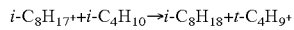
$i\text{-}C_8H_{17}{}^+ + i\text{-}C_4H_{10} \rightarrow i\text{-}C_8H_{18} + t\text{-}C_4H_9{}^+$ The desired product, the more highly branched trimethylpentane, is highly favored on reaction of 2-butenes, whereas the less branched dimethylhexane is formed in a much greater amount on reaction with 1-butene. It is therefore desirable to enrich 2-butenes relative to 1-butene in the input stream.

Stream f2 and ethene are fed into the metathesis stage G2), using 0.5 to 2 and preferably 0.9 to 1.2 mol of ethene per mole of 2-butene present in stream f2 (cis- and trans-2-butene). Stream f2, before being fed into the metathesis stage, can optionally be freed of any remaining residual amounts of 1,3-butadiene or other diolefins or alkynes by selective hydrogenation.

Various catalyst types are useful in principle for the metathesis, for example: a) rhenium-containing catalysts which are operated at temperatures in the range from 0 to 150° C., preferably in the range from 35 to 110° C., and b) tungsten-containing rhenium-free catalysts which are operated in the gas phase at temperatures of 200 to 600° C., preferably of 220 to 450° C.

The rhenium-containing catalysts preferably comprise at least 1% by weight of rhenium in oxidic form on a support consisting to an extent of at least 75% by weight of a high-surface area alumina, most preferably gamma-alumina. Especially preferred catalysts are those which have a rhenium content between 5% and 12% by weight and are supported on pure gamma-$Al_2O_3$. To enhance the activity, the catalysts may also additionally comprise dopants, for example oxides of Nb, Ta, Zr, Ti, Fe, Mn, Si, Mo, W, phosphate or sulfate. The catalysts have surface areas of at least 50 $m^2/g$, preferably at least 100 $m^2/g$, and a pore volume of at least 0.3 ml/g, preferably at least 0.4 ml/g. Suitable rhenium-containing catalysts are described, for example, in DE-A-102004009804, DE-A-102004009805 or DE-A-102004009803.

Suitable tungsten-containing rhenium-free catalysts comprise preferably at least 3% by weight of tungsten, at least partly in oxidic form, on a support selected from the group of aluminas, aluminosilicates, zeolites or, preferably, $SiO_2$. The catalysts preferably have a surface area of at least 50 $m^2/g$ and a pore volume of at least 0.3 ml/g, more preferably at least 0.5 ml/g. The activity, i.e. isomerization activity, can be altered by suitable doping, for example with alkali metal and alkaline earth metal compounds, $TiO_2$, $ZrO_2$, $HfO_2$, or with compounds or elements from the group consisting of Ag, Sb, Mn, W, Mo, Zn and Si.

It is known to those skilled in the art that all kinds of metathesis catalysts regularly have to be oxidatively regenerated. For this purpose, either a structure with fixed beds and at least two reactors is chosen, of which at least one reactor is always in regeneration mode, or alternatively a moving bed process can be executed, in which deactivated catalyst is discharged and regenerated externally.

The hydrocarbon stream formed in the metathesis stage is generally separated by commonly known distillation processes, optionally in a plurality of stages.

Stream f2 is fed into the oligomerization stage G3). Preferably, 2-butene is oligomerized to octenes and dodecenes. Nickel catalysts are generally used here.

Octenes and dodecenes are valuable intermediates which can especially be converted by hydroformylation and subsequent hydrogenation to nonanol and tridecanol respectively.

Nickel catalysts used are in particular those nickel-comprising catalysts that are known to bring about low oligomer branching, as described in DE 43 39 713 and WO 01/37989 and in the prior art references cited therein. Particular preference is given to catalysts comprising both sulfur and nickel as active component.

Most preferably, catalysts having different S:Ni ratios are combined. Advantageously, in the front reaction stage, a catalyst having an S:Ni ratio of <0.5 mol/mol, preferably a catalyst according to WO 01/37989 or DE 43 39 713, is used, and, in the rear reaction stage, a catalyst having an S:Ni ratio of >0.5 mol/mol, preferably a catalyst according to EP 272970, U.S. Pat. No. 3,959,400, FR 2641477 or U.S. Pat. No. 4,511,750 having an S:Ni ratio of >0.8, more preferably 1.0.

The abovementioned catalysts are used, for example, in processes as described, for example, in WO 99/25668 and WO 01/72670, which are hereby expressly incorporated by reference.

If the nickel catalyst is disposed in a plurality of fixed beds in the reactor, the feed can be divided and fed into the reactor at a plurality of points, for example upstream of a first fixed bed in flow direction of the reaction mixture and/or between individual fixed nickel catalyst beds. When a reactor cascade is used, for example, it is possible to supply the feed completely to the first reactor in the cascade or to distribute it over a plurality of feeds to the individual reactors in the cascade, as described for the case of a single reactor.

The oligomerization reaction generally takes place at temperatures of 30 to 280, preferably of 30 to 190 and especially of 40 to 130 C and a pressure of generally 1 to 300, preferably of 5 to 100 and especially of 10 to 50 bar. The pressure is appropriately chosen such that the feed is in supercritical form and especially in liquid form at the temperature set.

The reactor is generally a cylindrical reactor charged with the nickel catalyst; alternatively, it is possible to use a cascade composed of a plurality of, preferably two to three, reactors of this kind connected in series.

In the reactor or the individual reactors of the reactor cascade, the nickel catalyst may be disposed in a single fixed nickel catalyst bed or in a plurality thereof. It is also possible to use different nickel catalysts in the individual reactors in the cascade. In addition, different reaction conditions in terms of pressure and/or temperature may be established in the individual reactors of the reactor cascade within the abovementioned pressure and temperature ranges.

The front reaction stage should be operated at total olefin conversion >50%, preferably >70% and more preferably >90%, while the rear reaction stage assures the residual conversion, so as to result in an overall total olefin conversion of >91%, preferably >95% and more preferably >97%. This is also possible in principle using the catalyst in the front reaction stage alone, but this generally entails, in comparison to the invention, either high reaction temperatures which lead to relatively rapid catalyst deactivation or large catalyst volumes which would put in question the economic viability of the process.

The front and rear reaction stages may each consist of one or more series-connected reactors, as described in WO 99/25668 and 01/72670.

The resultant 2-butene oligomers can subsequently be recycled into the FCC plant, in which case 1-butene among other substances is in turn obtained by cracking and isomerization reactions. The overall result is thus an increased yield of 1,3-butadiene.

The unutilized n-butane is available for sale.

Typically, the butanes in stream f2, which are relatively inert in the dehydrogenation stage, are present in excess relative to the 2-butenes, as is advantageous, for example, for a downstream alkylation. Optionally, additional isobutane can be supplied in order to obtain a preferred ratio of reactants. The isobutane supplied in addition can also be provided by recycling of unreacted isobutane.

In a further step H), the stream f1 comprising 1,3-butadiene and the selective solvent is distilled and separated into a stream h1 comprising the selective solvent and a product gas stream h2 comprising 1,3-butadiene.

At the bottom of the distillation column, the stream h1 comprising the extractant is obtained, the composition of the extractant stream h1 corresponding essentially to the composition of the extractant on addition to the the particular extraction stage. The stream h1 comprising extractant can be recycled into the extractive distillation stage F).

In general, a portion of the extractant stream h1 is sent to an extractant purification stage, generally 0.01% to 0.5% of the total flow in the solvent circuit. For this purpose, the solvent can be drawn off continuously or batchwise from the bottom of a desorber column and distilled off continuously or batchwise. The distillation is preferably continuous. After the solvent has condensed, the solvent can be recycled into the extractive distillations.

1,3-Butadiene can be obtained via the top or in a sidestream in a desorption column. If the 1,3-butadiene is obtained via a side draw (as described, for example, in the Butadiene chapter in Ullmann's Encyclopedia of Industrial Chemistry 2012 in FIG. 3 for the so-called BASF process), the extraction solution thus drawn off is transferred into a desorption zone, the 1,3-butadiene being desorbed once again from the extraction solution and re-scrubbed. The desorption zone may be configured, for example, in the form of a scrubbing column having 2 to 30 and preferably 5 to 20 theoretical plates, and optionally a re-scrubbing zone having, for example, 4 theoretical plates. This re-scrubbing zone serves for recovery of the extractant present in the gas phase with the aid of a liquid hydrocarbon return stream, for which the top fraction is condensed beforehand. As internals, structured packings, trays or random packings are provided. The distillation is preferably performed at a bottom temperature in the range from 100 to 300° C., especially in the range from 150 to 200° C., and a top temperature in the range from 0 to 70° C., especially in the range from 10 to 50° C. The pressure in the distillation column is preferably in the range from 1 to 10 bar. In general, a reduced pressure and/or an elevated temperature exist in the desorption zone compared to the extraction zone.

The product of value stream obtained at the top of the column comprises generally 90% to 100% by volume of 1,3-butadiene, 0% to 10% by volume of 2-butene and 0% to 10% by volume of n-butane and isobutane. For further purification of the butadiene, a further distillation can be performed in accordance with the prior art.

Further impurities may be present in the stream h2 comprising 1,3-butadiene, for example propyne (methylacetylene), 1,2-butadiene, C5 hydrocarbons or possibly also small amounts of oxygenates. In one embodiment of the process, high boilers are removed from stream h2 in one or more further steps. This is effected, for example, by a two-stage distillation. In a first distillation, high boilers, for example propyne, can be removed via the top. In a second distillation of the bottom stream from the upstream column, 1,3-butadiene can be removed via the top, while high boilers, for example 1,2-butadiene or C5 hydrocarbons, remain in the bottom stream. The spectrum of impurities in stream h2 depends on various parameters. C5 hydrocarbons, 1,2-butadiene or propyne will generally get into stream h2 via stream b1. The spectrum of impurities in stream b1 also depends on the composition of the cracker feed used and the cracking severity. Oxygenates may possibly be entrained from the dehydrogenation stage into stream f1 and can possibly get into stream h2 via the latter. The spectrum of impurities in stream f1 also depends on the process conditions in the dehydrogenation stage and the separating performance in process stages D, Ea) and Eb). Process stage E) will generally be designed such that any oxygenates present in stream e1 are essentially removed in stream f1, in order to get into stream f2.

FIG. 1 shows a schematic of one embodiment of the process according to the invention. The labels therein have the following meanings:

A Stage for removal of isobutene
B Dehydrogenation stage
C Absorption and desorption stage
D Extractive distillation stage
E1 Unit for oligomerization
E2 Unit for metathesis and formation of propylene
E3 Alkylation
F Riser from an FCC plant, optionally the FCC plant that serves to produce input stream 1
1 C4 product fraction from an FCC plant, comprising 1,3-butadiene, 1-butene, cis- and trans-2-butene, isobutene, isobutane, n-butane
2 Methanol or ethanol
3 Stream comprising isobutene derivative, for example methyl tert-butyl ether or ethyl tert-butyl ether
4 Stream comprising 1-butene, 2-butenes, isobutane, n-butane
5 Product gas stream from the dehydrogenation
6 Uncondensable constituents
7 Stream comprising 1,3-butadiene, 1-butene, 2-butenes, isobutane, n-butane
8 Extraction solvent stream comprising 1,3-butadiene
9 Stream comprising 2-butenes, isobutane and n-butane, with or without 1-butene
10 Stream comprising alkylates, n-butane
11 Stream comprising propylene
12 Ethylene (optionally from the FCC plant that serves to produce input stream 1)
13a and 13b Stream comprising oligomers, preferably $C_8$ and $C_{12}$ oligomers

The invention claimed is:

1. A process for preparing 1,3-butadiene from n-butenes, the process comprising the steps of:
   A) providing an input gas stream that includes butanes, 1-butene, 2-butene and isobutene, with or without 1,3-butadiene, the input gas stream being from a fluid catalytic cracking plant;
   B) removing the isobutene from the input gas stream to provide a stream b that includes the butanes, the 1-butene and the 2-butene, with or without 1,3-butadiene;
   C) feeding the stream b and optionally an oxygenous gas and optionally water vapor into at least one dehydrogenating zone to dehydrogenate the 1-butene and the 2-butene to 1,3-butadiene, giving a product gas stream that includes the 1,3-butadiene, the butanes, the 2-butene and water vapor, with or without oxygen, with low-boiling hydrocarbons, with high-boiling secondary components, with or without carbon oxides and with or without inert gases, wherein at least 99% of the 1-butene present in stream b is converted in step C);
   D) cooling and compressing the product gas stream to provide at least one aqueous condensate stream d1 and a gas stream d2 comprising the 1,3-butadiene, the butanes, the 2-butene and the water vapor, with or without oxygen, with low-boiling hydrocarbons, with or without carbon oxides and with or without inert gases;
   Ea) removing uncondensable and low-boiling gas constituents comprising low-boiling hydrocarbons, with or without oxygen, with or without carbon oxides and with or without inert gases, as gas stream e2 from the gas stream d2 by absorbing the $C_4$ hydrocarbons comprising the 1,3-butadiene, the butanes and the 2-butene, in an absorbent to provide an absorbent stream laden with the $C_4$ hydrocarbons and the gas stream e2, and
   Eb) desorbing the $C_4$ hydrocarbons from the laden absorbent stream to provide a $C_4$ hydrocarbon stream e1;
   F) separating the $C_4$ hydrocarbon stream e1 by extractive distillation with a 1,3-butadiene-selective solvent to provide a stream f1 that includes the 1,3-butadiene and the selective solvent and a stream f2 that includes the butanes and the 2-butene;
wherein the stream f2 obtained in step F) is directly fed to and converted further in one or more of steps G1), G2) or G3) by
   G1) alkylating 2-butene with butanes to give isooctanes;
   G2) subjecting 2-butene to olefin metathesis with ethene to give propene; or
   G3) oligomerizing 2-butene.

2. The process according to claim 1 wherein the dehydrogenation in step C) is performed as an oxidative dehydrogenation.

3. The process according to claim 1, wherein $C_8$ and $C_{12}$ oligomers of 2-butene are prepared in step G3).

4. The process according to claim 3, wherein the 2-butene oligomers obtained in step G3) are fed into a fluid catalytic cracking plant.

5. The process according to claim 1, wherein in step D) the cooling and the compressing comprises
   Da) contacting the product gas stream with a coolant and condensing at least a portion of the high-boiling secondary components; and
   Db) compressing the remaining product gas stream in at least one compression stage to provide at least one aqueous condensate stream d1 and the gas stream d2.

6. The process according to claim 1, wherein the absorbent of step Ea) is an aromatic hydrocarbon solvent.

7. The process according to claim 1, wherein the 1,3-butadiene-selective solvent comprises N-methylpyrrolidone.

8. The process according to claim 1, comprising the step of:
   H) distilling the stream f1 comprising 1,3-butadiene and the selective solvent from stage F) and separating it into a stream h1 comprising the selective solvent and a product gas stream h2 comprising 1,3-butadiene.

* * * * *